(12) United States Patent
Kfir

(10) Patent No.: US 10,149,740 B2
(45) Date of Patent: Dec. 11, 2018

(54) METHOD AND SYSTEM FOR DENTAL IMPLANTATION

(75) Inventor: Pinchas Kfir, Petach Tikva (IL)

(73) Assignee: Zeev Implants Ltd., M.P. Misgav (IL)

( * ) Notice: Subject to any disclaimer, the term of this patent is extended or adjusted under 35 U.S.C. 154(b) by 684 days.

(21) Appl. No.: 13/055,465

(22) PCT Filed: Jul. 22, 2009

(86) PCT No.: PCT/IL2009/000717
§ 371 (c)(1),
(2), (4) Date: Apr. 6, 2011

(87) PCT Pub. No.: WO2010/010558
PCT Pub. Date: Jan. 28, 2010

(65) Prior Publication Data
US 2011/0189634 A1 Aug. 4, 2011

Related U.S. Application Data

(60) Provisional application No. 61/083,196, filed on Jul. 24, 2008.

(51) Int. Cl.
*A61C 8/00* (2006.01)
(52) U.S. Cl.
CPC .......... *A61C 8/0018* (2013.01); *A61C 8/0025* (2013.01); *A61C 8/0042* (2013.01)
(58) Field of Classification Search
CPC ... A61C 8/0022; A61C 8/0068; A61C 8/0018; A61C 8/005; A61C 8/0075; A61C 8/0037; A61C 13/225
USPC .................................. 433/172–176
See application file for complete search history.

(56) References Cited

U.S. PATENT DOCUMENTS

| 514,135 | A | | 2/1894 | Sidney, II |
| 3,679,531 | A | | 7/1972 | Wienand |
| 5,141,435 | A | * | 8/1992 | Lillard ................. A61C 8/0033 433/176 |
| 5,542,847 | A | | 8/1996 | Margulies |
| 6,250,922 | B1 | * | 6/2001 | Bassett .................. A61C 8/005 433/172 |
| 7,281,926 | B2 | * | 10/2007 | Yakir ..................... A61C 8/001 433/173 |

(Continued)

FOREIGN PATENT DOCUMENTS

| DE | 102004017344 | 11/2005 |
| EP | 1030622 B2 | 5/2014 |
| WO | 03005928 | 1/2003 |

OTHER PUBLICATIONS

Persson LG, Osseintegration following treatment of peri-implantitis and replacement of implant components, Journal of Clinical Periodontology, Accepted for publication Apr. 22, 2000, ISSN 0303-6979, Munksgaard, 2001, Denmark.

*Primary Examiner* — Matthew Nelson
(74) *Attorney, Agent, or Firm* — Roach Brown McCarthy & Gruber, P.C.; Kevin D. McCarthy

(57) ABSTRACT

A modular dental implant that includes multiple segments that are connected to each other in a sequential manner to form the modular dental implant; wherein the multiple segments comprise an abutment, at least one implant body segment and at least one other segment; wherein the at least one other segment is an implant apex, an implant neck or at least one implant body segment.

19 Claims, 14 Drawing Sheets

(56) References Cited

U.S. PATENT DOCUMENTS

| | | | |
|---|---|---|---|
| 7,699,613 B2* | 4/2010 | Niznick | A61C 8/0001 |
| | | | 433/174 |
| 2003/0013068 A1* | 1/2003 | Gittleman | A61C 8/005 |
| | | | 433/173 |
| 2004/0152047 A1* | 8/2004 | Odrich | A61C 8/005 |
| | | | 433/173 |
| 2005/0208453 A1 | 9/2005 | Balfour et al. | |
| 2006/0121417 A1 | 6/2006 | Scommegna et al. | |
| 2006/0183078 A1* | 8/2006 | Niznick | A61C 8/0001 |
| | | | 433/173 |
| 2007/0099153 A1* | 5/2007 | Fromovich | A61C 8/0022 |
| | | | 433/174 |
| 2007/0148621 A1* | 6/2007 | Yakir | A61C 8/001 |
| | | | 433/173 |
| 2007/0275351 A1* | 11/2007 | Park | A61C 8/008 |
| | | | 433/174 |
| 2008/0153064 A1* | 6/2008 | Han | A61C 8/0022 |
| | | | 433/174 |
| 2008/0227058 A1 | 9/2008 | Karmon | |
| 2009/0061388 A1* | 3/2009 | Collins | A61C 8/0006 |
| | | | 433/174 |
| 2010/0003638 A1* | 1/2010 | Collins | A61C 8/0012 |
| | | | 433/174 |
| 2010/0330531 A1* | 12/2010 | Olsson | A61C 8/005 |
| | | | 433/173 |
| 2012/0156645 A1 | 6/2012 | Jacoby | |

\* cited by examiner

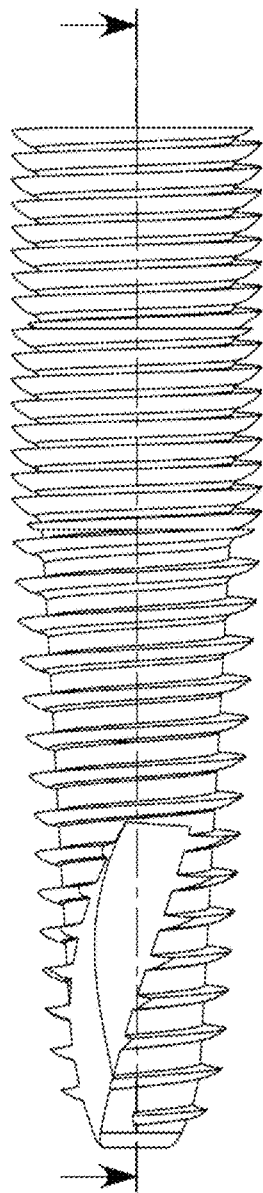
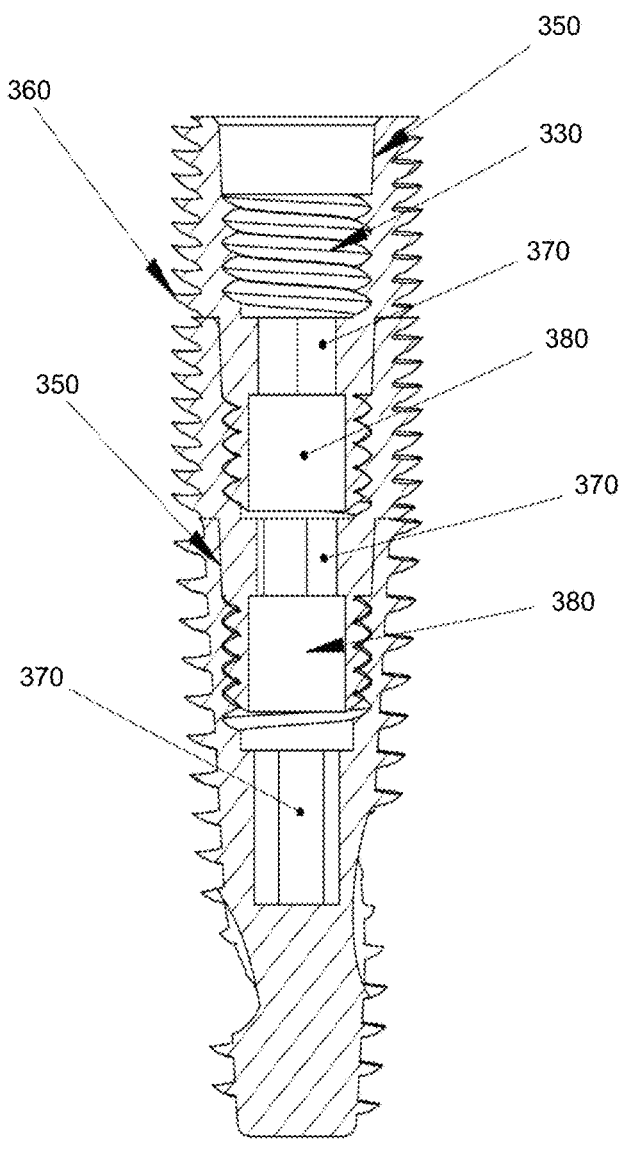
FIG. 10A
FIG. 10B

METHOD AND SYSTEM FOR DENTAL IMPLANTATION

CROSS REFERENCE TO RELATED APPLICATIONS

This application is a national phase application of PCT/IL2009/000717 (and entitled METHOD AND SYSTEM FOR DENTAL IMPLANTATION) which claims the benefit of U.S. provisional Ser. No. 61/083,196 filed on 24 Jul. 2008 (and entitled METHOD AND SYSTEM FOR DENTAL IMPLANTATION), both applications are incorporated in their entirety herein by reference.

FIELD OF THE INVENTION

The present invention relates to medical dental implants used to form root analogues for the attachment of dental prostheses, and more particularly, to extendable dental implants.

BACKGROUND OF THE INVENTION

Dental implants are commonly used for artificial replacements of teeth roots. A dental implant is usually constructed from an implant body and from an abutment (or other type of dental prosthetic attachment) for supporting prosthesis or like dental solutions. The bottom portion of the implant usually includes an apex.

It is noted that dental implants of various sizes are utilized by each dental professional, which requires a whole variety of implants to be available for every single surgeon. Prior art dental implants are not capable of being extended or shortened according to changing clinical requirements—both during the dental implantation and further in the treatment—which affects the quality of the restoration, may hamper the restoration, and may hurt (in different degrees of severity) in a periodontal supporting structure of the dental implant, and/or in an environment of the dental implant.

There is a growing need to provide reliable and simple means of constructing dental implants.

SUMMARY OF THE INVENTION

A modular dental implant is provided. The modular dental implant includes multiple segments that are connected to each other in a sequential manner to form the modular dental implant; wherein the multiple segments comprise an abutment, at least one implant body segment and at least one other segment; wherein the at least one other segment is an implant apex, an implant neck or at least one implant body segment.

A method for a dental implantation, includes: selecting multiple segments that once connected form a modular dental implant; wherein the multiple segments comprise an abutment, at least one implant body segment and at least one other segment; wherein the at least one other segment is an implant apex, an implant neck or at least one implant body segment; attaching the multiple segments to each other to provide the modular dental implant; wherein the modular dental implant is of a desired length; inserting at least a portion of the modular dental implant into a jaw; and connecting an abutment to an upper segment of the modular dental implant.

An extraction kit for extracting segments out of a modular dental implant, includes: multiple extractors for extracting an upper segment of the modular dental implant; and an extractor selection gauge for selecting a required extractor of the multiple extractors.

A method for extracting a segment of a modular dental implant, includes: inserting an extractor selection gauge into an opening of at least partially assembled modular dental implant, until a bottom of the extractor selection gauge touches a bottom of the at least partially assembled modular dental implant; wherein the extractor selection gauge includes multiple denotations located in different distances from the bottom of the extractor selection gauge that match to different extractors of an extraction kit; and selecting an extractor of the extraction kit in response to a denotation, out of the multiple denotations, indicated on the extractor selection gauge.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 10A is a front view and FIG. 10B is a longitudinal cross sectional view of a constructed modular dental implant, according to an embodiment of the invention;

Figure 1:
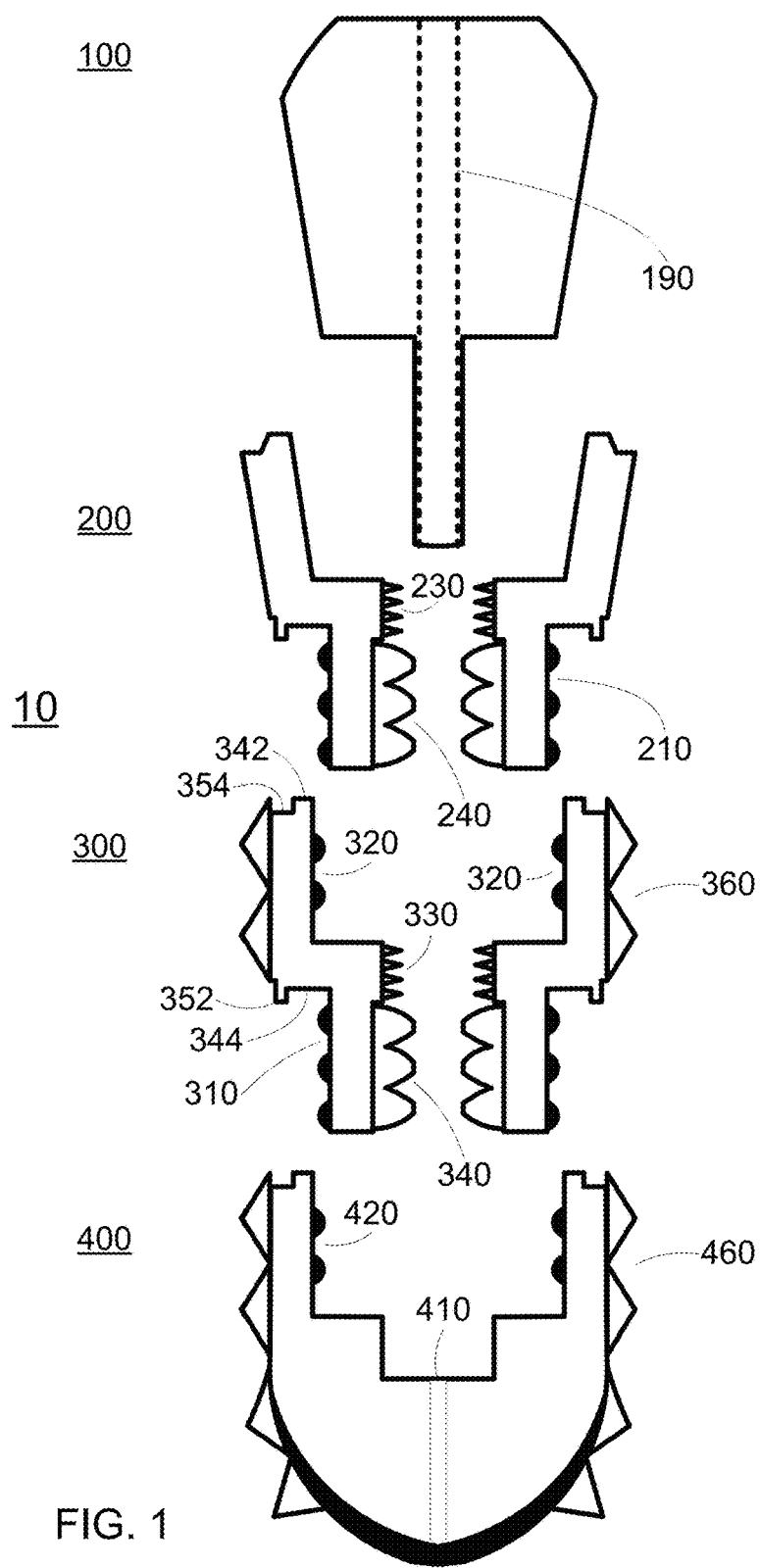
FIG. 1 is a longitudinal cross sectional view of segments that construct a modular dental implant, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following detailed description utilizes the terms top, upper and bottom in relation to the illustrations in the different figures, wherein the term bottom also refers to a deepest segment of the implant (when implanted in the jaw) and the term top or upper refers to the outer segment of the implant.

A modular dental implant is provided. It includes multiple segments that are connected to each other in a sequential manner to form the modular dental implant. The multiple segments may be connected to each other in a coaxial manner wherein an upper portion of one segment is located above an upper portion of the other. The number of segments per modular dental implant can be selected in view of a desired length of the modular dental implant. The modular dental implant is modular in the sense that each segment can be connected to one or two segments without substantially changing a shape of the segments or performing additional adaptations. Medical dental implants of different lengths can be built from different numbers of the same segments. A medical dental implant can be lengthened by adding one or more segments and can be shortened by removing one or more segments.

Modular dental implants can include an abutment or any other dental prosthetic attachment, at least one implant body segment and at least one other segment. The at least one other segment is an implant apex, an implant neck or at least one implant body segment. For example—a modular dental implant can include multiple implant body segments. Yet for another example—a modular dental implant can include one or more implant body segments and an implant apex. Yet for a further example—a modular dental implant can include one or more implant body segments and an implant neck. It is noted that a modular dental implant can include one or more implant body segments, an implant apex and an implant neck.

FIG. 1 is a longitudinal cross sectional view of multiple segments that construct a modular dental implant 10, according to an embodiment of the invention. Modular dental implant 10 can be constructed using different amount of implant body segments 300 (e.g. two implant body segments are used in modular dental implant 10 illustrated in FIG. 2), to achieve modular dental implants 10 of different lengths, so as to suit different dental needs. Each implant body segment 300 is shaped to be connected between two other segments.

It is noted that conveniently, modular dental implant 10 and the different components thereof are of substantially rotational symmetry, albeit some parts of modular dental implant 10 or of the different components thereof may deviate from such symmetry. E.g. according to some embodiments of the invention, helical threads are applied to some components of modular dental implant 10, so as to allow screwing of one component into another, which obviously deviate from strict rotational symmetry.

Figure 2:
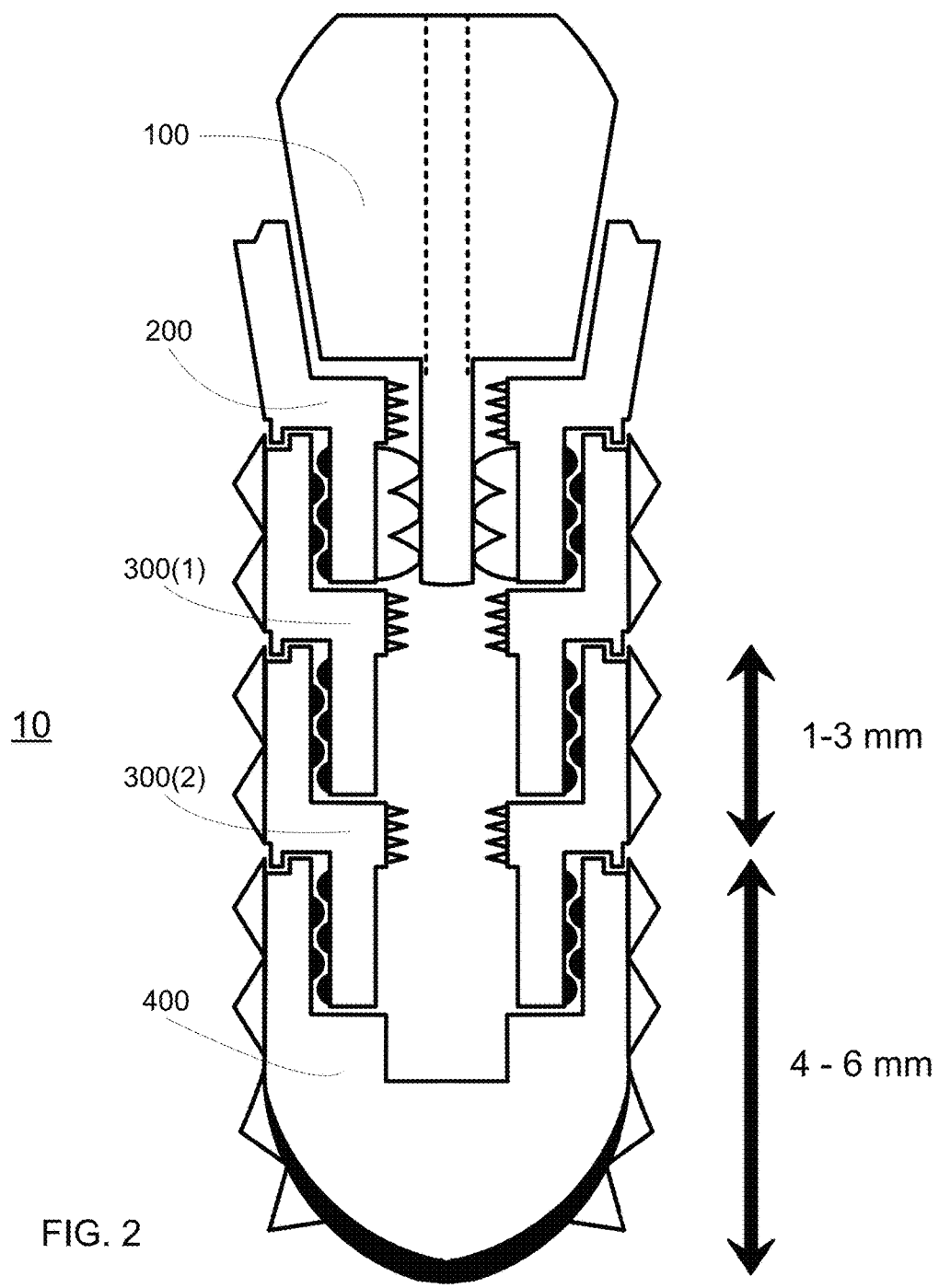
FIG. 2 is a longitudinal cross sectional view of a modular dental implant after being constructed, according to an embodiment of the invention.

Modular dental implant 10 includes an implant apex 400, that is adapted to be inserted into a jaw (e.g. into a drill hole made by osteotomy or by precision drilling) and to support at least one implant body segment 300. Each implant body segment 300 includes an external fastening surface 310 and an internal fastening surface 320, conveniently having a substantially cylindrical shape, so that a first implant body segment 300 could be fastened into a second adjacent implant body segment 300, by fastening the external fastening surface 310 of the first implant body segment 300(1) into the internal fastening surface 320 of the second adjacent implant body segment 300(2) (e.g. as illustrated in FIG. 2).

At least one of the internal and external fastening surfaces 310 and 320 may include a helical thread into which a fastening surface of another implant body segment 300 is screwed. According to another embodiment, the internal and external surfaces have a detachment prevention texture that generated friction, which prevents the external fastening surface 310 of the first implant body segment 300 from detaching from the internal fastening surface 320 of the second implant body segment 300, wherein the fastening surfaces are then usually design to offer sufficient friction, e.g. by having a detachment prevention texture that provides friction.

It is noted that at least one of the fastening surfaces may be composed from several portions that may slightly change the distance from one another and from a rotational axis of the implant body segment 300, so as to force the external fastening surface 310 of the first implant body segment 300 into the internal fastening surface 320 of the second implant body segment 300.

According to an embodiment of the invention, the fastening between the fastening surfaces 310 and 320 of adjacent implant body segments 300 is achieved by friction.

Figure 4:
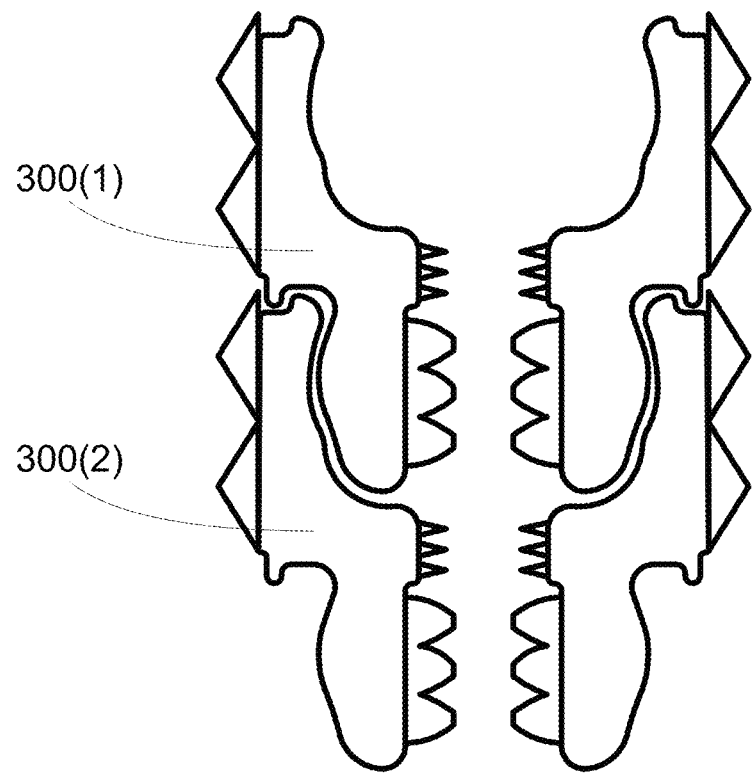
FIG. 4 is a longitudinal cross sectional view of segments that construct a modular dental implant, according to another embodiment of the invention.

According to an embodiment of the invention, a diameter of external fastening surface 310 is somewhat larger than a diameter of internal fastening surface 320 (e.g. as illustrated in FIG. 4), so that a first implant body segment 300 could be fastened to a second implant body segment 300, by forcing external fastening surface 310 of the first implant body segment 300 to the internal fastening surface 320 of the second implant body segment 300. It is noted that those fastening mechanism may be used for fastening other components of modular dental implant 10 to each other as well, mutatis mutandis.

Figure 6:
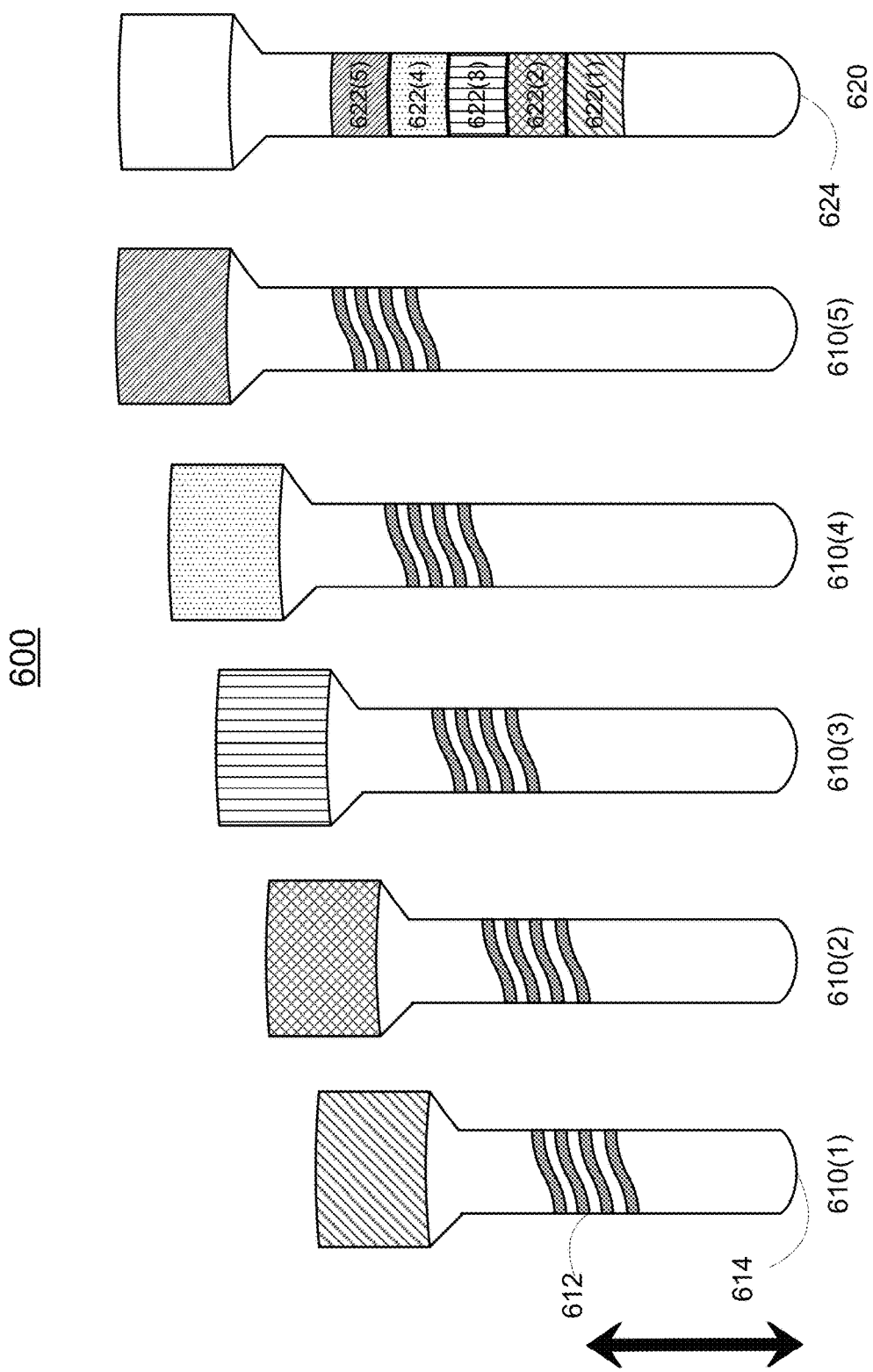
FIG. 6 illustrates an extraction kit for extracting an implant body segment, according to an embodiment of the invention.
Figure 7:
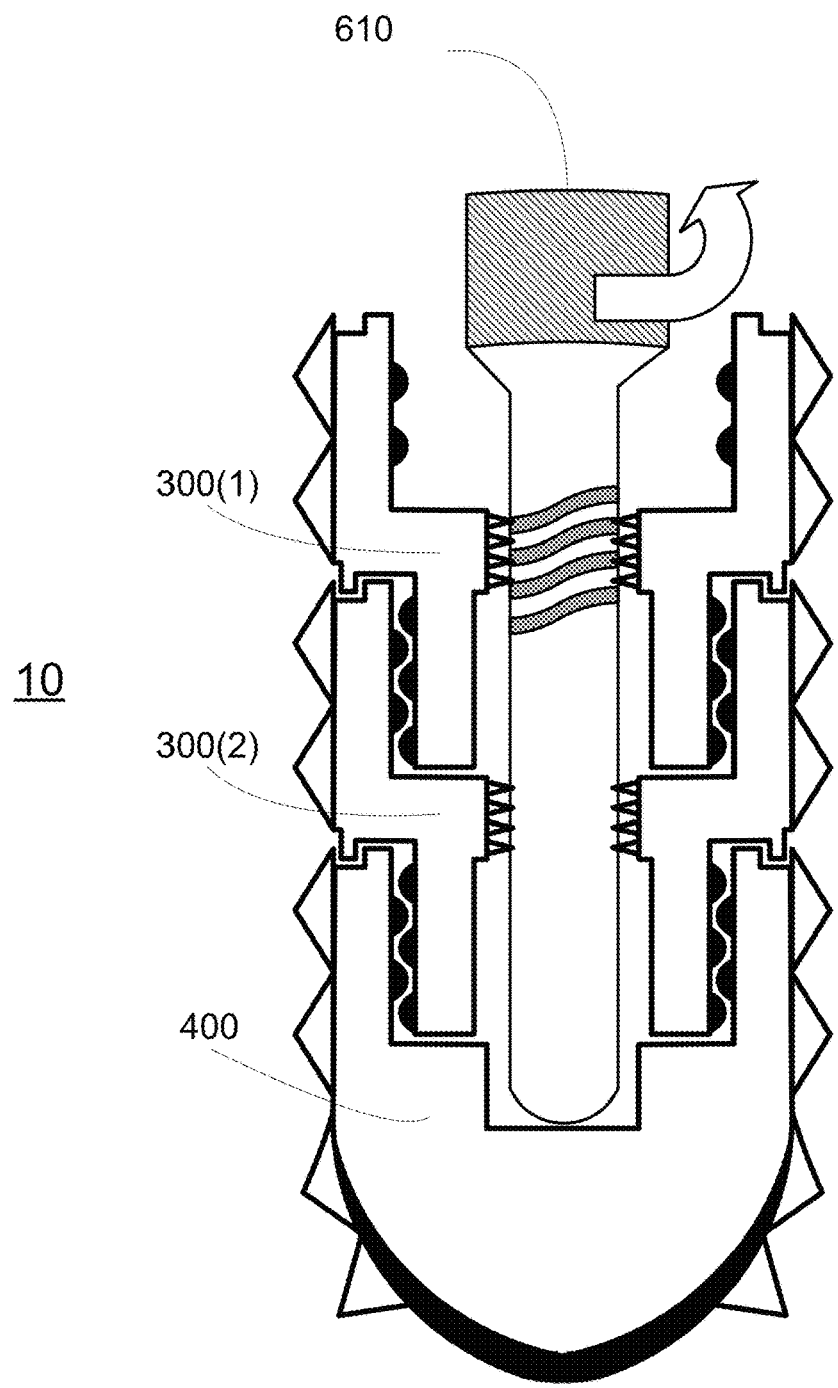
FIG. 7 illustrates a usage of the extraction kit during the extraction of an implant body segment, according to an embodiment of the invention.

Conveniently, implant body segment 300 further includes extracting helical threads 330, in a shape of a helical thread, which are used for extraction of the implant body segment 300 from the jaw of the patient, and/or from another implant body segment to which it is currently fastened, e.g. as disclosed in FIG. 6 and FIG. 7.

According to an embodiment of the invention, implant body segment 300 further includes at least one circumferential tongue (e.g. the tongues denoted 342 and 352) that is shaped so as to fit into a groove in an adjacent implant body segment 300 (e.g. groove 344 or 354, respectively), so as to further secure the two adjacent implant body segments 300. It is noted that in other embodiments of the invention, different joining means may be implemented such as different types of slices, rebates, dados, etc.

Figure 14:
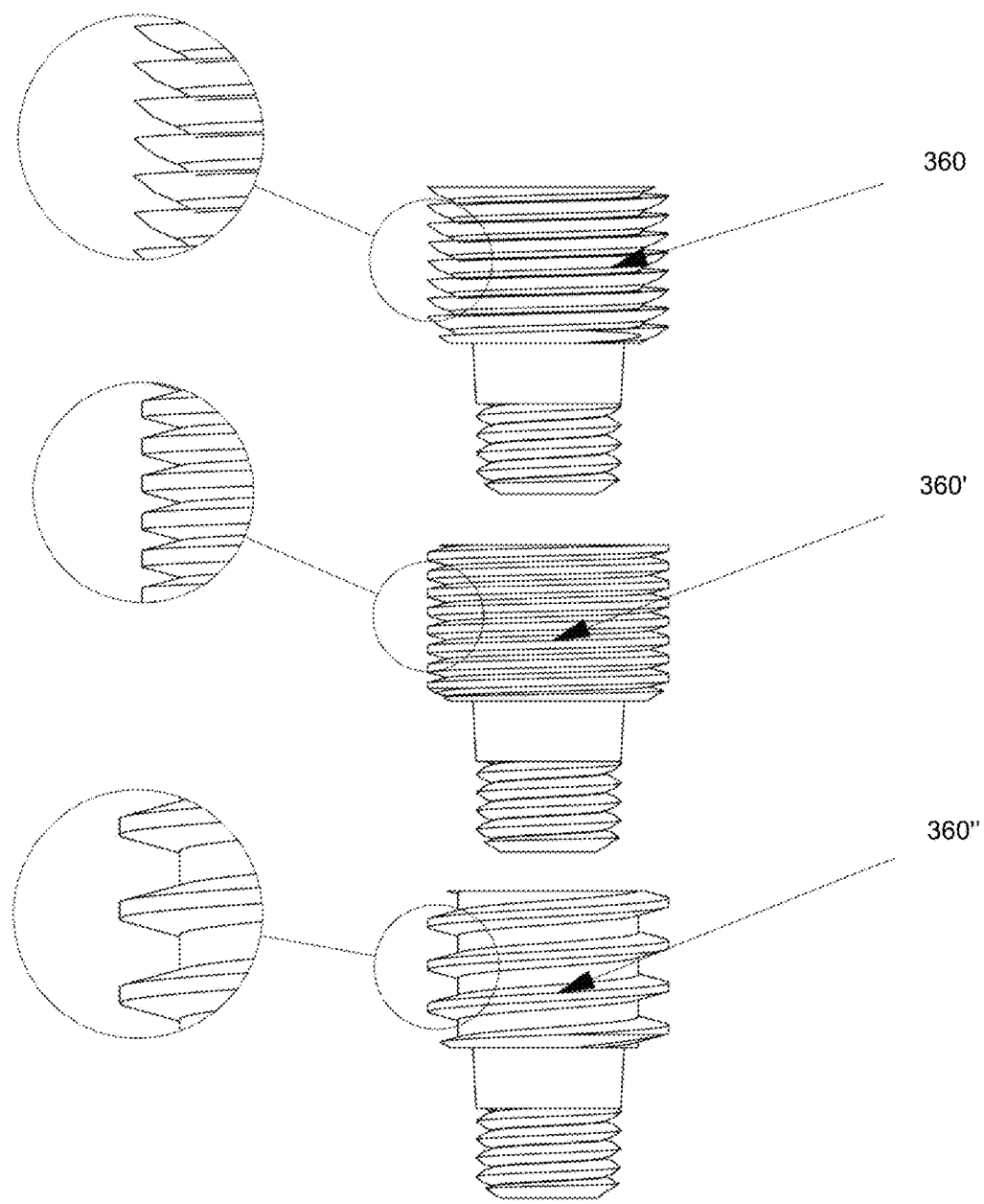
FIG. 14 is a front view of segments with different threads, according to another embodiment of the invention.

According to an embodiment of the invention, implant body segment 300 further includes external threads 360, that are adapted to assist in an insertion of modular dental implant 10 into the drilled jaw, and/or to prevent undesired extraction of modular dental implant 10 from the jaw. It is noted that, according to an embodiment of the invention, external threads 360 are tilted in relation to a longitudinal axis of the modular dental implant 10 (or otherwise shaped), so as to facilitate the insertion of the modular dental implant 10 into the jaw, and to prevent unintentional extraction therefrom. The threads can be spaced by various gaps, wraps the surface in various slopes, have various inclinations and have various intenseness. External threads 360 might also have different shapes as illustrated in FIG. 14. Some threads may be microscopic while other might be macroscopic. Different shaped threads may co-exist in different part of the same modular dental implant 10.

It is noted that external threads (which may be external threads 360 or other external threads) may also, according to an embodiment of the invention, be implemented for facilitating an osseointegration of modular dental implant 10 (or portions thereof) in the bone.

According to an embodiment of the invention, implant body segment 300 further includes internal abutment mount 340, that is adapted to provide support for an abutment 100 when the latter is connected to other components of modular dental implant 10, and/or to prevent (or to limit) undesired movements of abutment 100 in relation to modular dental implant 10. It is noted that if internal abutment mounts 340 are implemented, some internal abutment mounts 340 may not provide support (e.g. of one or more bottom implant body segments 300).

Regarding all the threads used in different embodiments of the invention, in different components of modular dental implant 10, it is noted that while illustrated symmetrically in different sides of the modular dental implant 10, naturally, the threads are conveniently of helical shape.

Referring to implant apex 400, implant apex 400 conveniently includes internal fastening surface 420 for fastening an implant body segment 300 to implant apex 400, by fastening the external fastening surface 310 of the implant body segment 300 to the internal fastening surface 420 of the implant apex 400 (e.g. as illustrated in FIG. 2). Conveniently, internal fastening surface 420 is substantially similar to the internal fastening surface 320 of the at least one implant body segments 300.

According to an embodiment of the invention, implant apex 400 further includes external threads 460, that are adapted to assist in an insertion of modular dental implant 10 into the drilled jaw, and/or to prevent undesired extraction of modular dental implant 10 from the jaw. It is noted that, according to an embodiment of the invention, external threads 460 are tilted in relation to a surface of implant apex 400 and/or in relation to the longitudinal axis of the modular dental implant 10 (or otherwise shaped), so as to facilitate the insertion of the modular dental implant 10 into the jaw, and to prevent unintentional extraction therefrom. It is noted that external threads (which may be external threads 460 or other external threads) may also, according to an embodiment of the invention, be implemented for facilitating an osseointegration of modular dental implant 10 (or portions thereof) in the bone.

According to an embodiment of the invention, implant apex 400 further include extractor supporting surface 410 for providing support to an extractor during an extraction of an implant body segment 300 or of other component of modular dental implant 10, as described in FIG. 6 and FIG. 7.

It is noted that, according to another embodiment of the invention, a bottom implant body segment 300 could also serve as an implant apex 400 (wherein the implant body segments are then usually accordingly shaped). That is, according to an embodiment of the invention, an implant apex 400 that is different from the implant body segments 300 of modular dental implant 10 is not used, and the bottommost implant body segment 300 may provide some or all of the functionalities disclosed in relation to implant apex 400.

Modular dental implant 10 may also includes implant neck 200, that is fastened to the upper implant body segment 300, and facilitate connection of abutment 100 to a body of modular dental implant 10 (which includes the implant apex 400 and one or more substantially identical implant body segments 300). Implant neck 200 is shaped to fit a implant body segment at the lower end thereof.

It should be noted that the terms top and bottom in relation to the disclosure generally refers to the illustrations in the different figures, wherein the term bottom also refers to a deepest segment of the implant (inside the jaw) and the term top (or upper) refers to a segment of the implant that is located at an opposite end of the medical dental implant. Naturally the implant neck 200 may be situated lower than the at least one implant body segments 300, e.g. when modular dental implant 10 are used in maxillae.

It is further noted that modular dental implant 10 may provide support for different types of dental prosthetic attachments other then abutments, and that it would be clear to a person who is skilled in the art that wherever the term abutment is used in relation to the invention, other types of dental prosthetic attachments may be implemented as well, mutatis mutandis.

Conveniently, implant neck 200 includes external fastening surface 210, for fastening the implant neck 200 to the upper implant body segment 300, to which it is adjacent. Conveniently, external fastening surface 210 is substantially identical to the external fastening surfaces 310 of the implant body segments 300. Similarly, conveniently implant neck 200 includes extracting helical threads 230 for the extraction of implant neck 200 when required, which are substantially similar to the extracting helical threads 330 of the implant body segments 300.

According to an embodiment of the invention, implant neck 200 further includes internal abutment mount 240, that is adapted to provide support for abutment 100 when the latter is connected to the implant neck 200, and/or to prevent (or to limit) undesired movements of abutment 100 in relation to implant neck 200.

Conveniently, abutment 100 includes screw access hole 190, for allowing a screwing of a fastening screw (not shown), for fastening abutment 100 (and/or other components of modular dental implant 10) to another component of modular dental implant 10, such as implant neck 200 or implant apex 400. It is noted that the component of modular dental implant 10 into which the fastening screw is screwed in for fastening usually includes dedicated threads (not illustrated).

It is noted that, according to embodiment of the invention, no implant neck 200 is used for modular dental implant 10, and a upper implant body segment 300 fulfils the functionalities of facilitate the connection of abutment 100 to a body of modular dental implant 10 (which includes the implant apex 400 and one or more substantially identical implant body segments 300), thus obviating a need for implant neck 200. It is noted that, according to such an embodiment of the invention, the implant body segments 300 are then usually accordingly shaped.

It is further noted that using a upper body segment 300 for connecting to abutment 100 instead of an implant neck 200 may facilitate more flexibility and ease of utilization for connecting or removing additional body segments 300 at future times, among other advantages.

FIG. 2 is a longitudinal cross sectional view of modular dental implant 10, constructed from a row of segments, according to an embodiment of the invention. The modular dental implant 10 of FIG. 2 includes two implant body segments 300, denoted 300(1) and 300(2), but it is noted that additional or less implant body segments 300 may be used, if a modular dental implant 10 of different length is required.

Conveniently, the effective length of each of the implant body segments 300 is a given length between 1 and 3 millimeters, although it is clear that other lengths could also be used.

Conveniently, the effective length of the implant apex 400 is a about 4 to 6 millimeters, although it is clear that other lengths could also be used.

Figure 3:
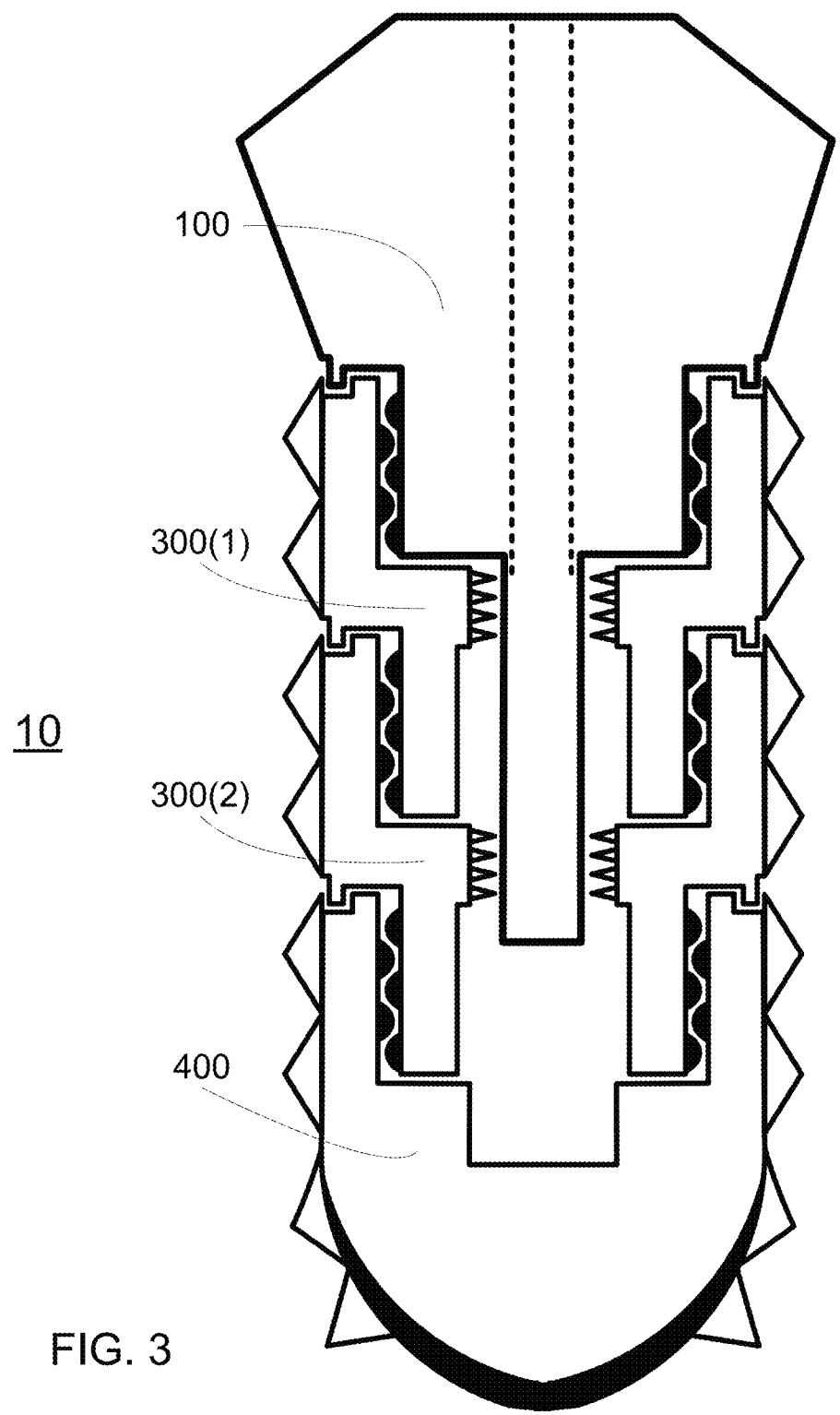
FIG. 3 is a longitudinal cross sectional view of a modular dental implant after being constructed, according to another embodiment of the invention.

FIG. 3 is a longitudinal cross sectional view of modular dental implant 10, according to an embodiment of the invention. It is noted that no implant neck 200 is utilized in this embodiment and a bottom portion of abutment 100 is shaped to fit into a top portion of implant body segment 300, e.g. as disclosed above in relation to implant body segment 300.

Figure 5:
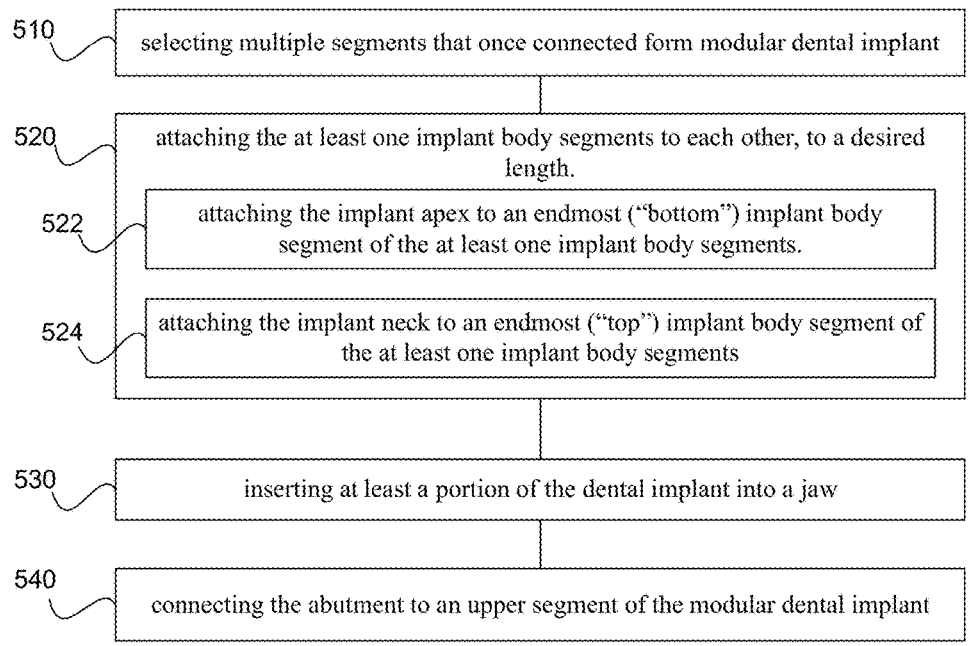
FIG. 5 illustrates a flow diagram of a method for dental implantation.

FIG. 5 illustrates a flow diagram of a method 500 for a dental implantation, according to an aspect of the invention.

Method 500 starts with a stage 510 of selecting multiple segments that once connected form modular dental implant 10. The multiple segments include: an abutment, at least one implant body segment and may include an implant apex and an implant neck.

Stage 510 is followed by stage 520 of attaching at least one implant body segments to each other, to a desired length.

Stage 520 may include a stage 522 of attaching the implant apex to an endmost ("bottom") implant body segment of the at least one implant body segments. Stage 522 can be carried out before, during or following the attaching the at least one implant body segments to each other. The attaching of one implant body segment to another (if required—i.e. if there is more than one implant body segment) can be done by screwing a portion of the at least one implant body segment to a portion of the other, by forcing such portion into a portion of the other implant body segment, or by other ways known in the art—that match the structure and operation of the modular dental implant.

Stage 520 may include a stage 524 of attaching the implant neck to an endmost ("top") implant body segment of the at least one implant body segments. It is noted that if only one implant body segment is used, then the implant neck and the implant apex are connected to different ends of a single implant body segment, but that otherwise those components are connected to implant body segments that are located in different ends of the group of implant body segments when the latter are connected to each other.

Stage 520 can be carried out after stage 510 or in parallel to stage 510.

Stage 520 is followed by stage 530 of inserting at least a portion of the modular dental implant into a jaw (a portion that includes at least the at least one implant body segments, when the latter are connected to each other, and the implant apex). The insertion may be by way of screwing the at least a portion of the modular dental implant into a drill formed in the jaw, by forcing the at least a portion of the modular dental implant into the drill formed in the jaw, or in other manners that are known in the art.

Stage 530 is followed by stage 540 of connecting the abutment (or other type of attachment) to an upper segment of the modular dental implant, such as the implant neck or an implant body segment that serves as an implant neck. The connecting of the abutment is usually carried out by screwing a fastening screw into at least one component of the modular dental implant, and through at least one other component (such as the abutment and potentially also other components).

It is noted that aforementioned different stages of the method may be carried out in varying order, according to different embodiments of the invention. Usually those stages when taken as a group are followed by anchoring a crown or other prosthetic restoration elements to the modular dental implant.

FIG. 6 illustrates an extraction kit 600 that includes multiple extractors 610(1) through 600(5) for extracting implant body segments 300 of the modular dental implant 10 (and potentially, also other components thereof), as well as extractor selection gauge 620 that is used for selecting the required extractor 610 for extracting the outermost implant body segment 300, according to an embodiment of the invention.

Each of the extractors 610 includes extracting helical thread 612. In each extractor 610, extracting helical thread 612 is located in a different distance from the extractor bottom 614. When rotating the extractor 610 (As illustrated in FIG. 7, for example), the extractor that is being forced against the implant apex 410 extracts the respective implant body segment 300 out.

Conveniently, each of the extractors 610 is denoted by a unique denotation. e.g. different color (or other pattern or texture), e.g. of the handle as illustrated in FIG. 6.

The extractor selection gauge 620 includes matching denotations 622 (e.g. colors) in different distances from a bottom 624 of extractor selection gauge 620. Thus, each matching denotation 622 is located in a dedicated distance from bottom 624 of extractor selection gauge 620.

When extractor selection gauge 620 is inserted into an at least partially assembled modular dental implant 10, until bottom 624 thereof touches extractor supporting surface 410 of Implant apex 400, it indicated the specific extractor 610 of the extraction kit 500 that is required to extract the top most implant body segment 300.

Although FIG. 6 illustrates extractors 610 as having extracting helical thread 612, according to other embodiments of the invention, extractors 610 may have hex shape that is used for the extraction or any other shape that is adapted for extraction.

Figure 8:
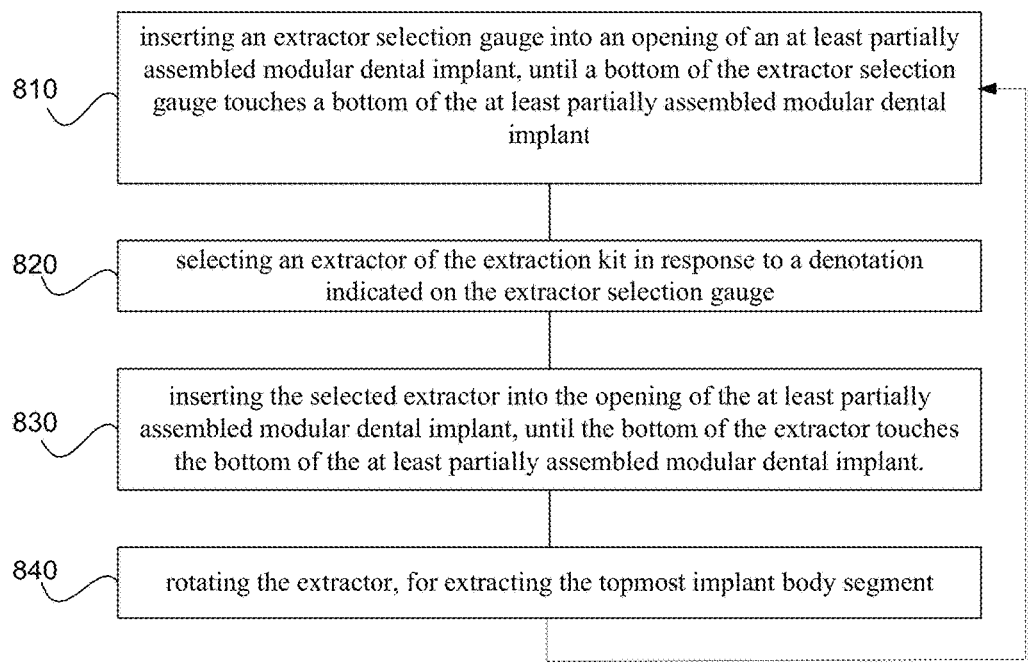
FIG. 8 illustrates a flow diagram of a method for extracting implant body segments.

FIG. 8 illustrate a flow diagram 800 for extracting implant body segments, according to an embodiment of the invention.

Method 800 starts with a stage 810 of inserting the extractor selection gauge into an opening of an at least partially assembled modular dental implant, until the bottom of the extractor selection gauge touches a bottom of the at least partially assembled modular dental implant. The bottom of the at least partially assembled modular dental implant can be extractor supporting surface 410 of Implant apex 400. The at least partially assembled modular dental implant includes at least one implant body segment. The extractor selection gauge includes multiple denotations in different distances from a bottom of the extractor selection gauge that match to different extractors of an extraction kit.

Stage 810 is followed by stage 820 of selecting an extractor of the extraction kit in response to a denotation indicated on the extractor selection gauge (e.g. the lowermost revealed denotation).

Stage 820 is followed by stage 830 of inserting the selected extractor into the opening of the at least partially assembled modular dental implant, until the bottom of the extractor touches the bottom of the at least partially assembled modular dental implant.

Stage 830 is followed by stage 840 of rotating the extractor, for extracting the upper implant body segment. Stage 840 can be followed by stage 810 if there more segments left to be extracted.

Figure 9:
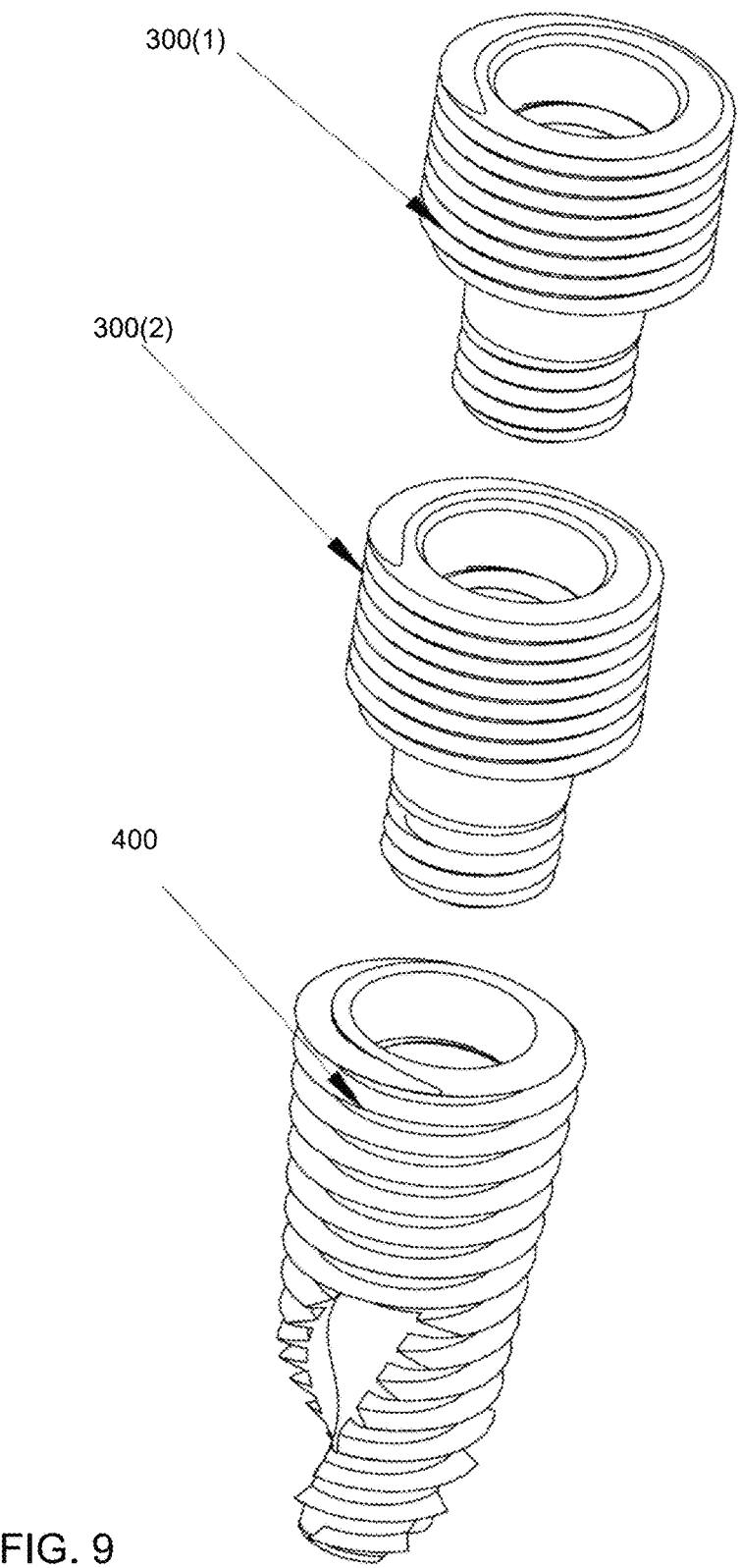
FIG. 9 is a perspective view of segments that construct a modular dental implant, according to an embodiment of the invention.

FIG. 9 is a perspective view of segments that construct a modular dental implant. FIG. 9 illustrates two implant body segment 300(1) and an apex 400.

FIG. 10A is a front view and FIG. 10B is a longitudinal cross sectional view of a modular dental implant that was constructed using the segments described in FIG. 9. FIG. 10B illustrates: a sealing surface 350, and internal hex 370, internal screwdriver pass way 380, external threads 360 and extracting helical threads 330.

Sealing surface 350 might be treated by using different methods: sand spraying, acid treatment and other methods known in the art. Different treated sealing surfaces may co-exist in different parts of the same modular dental implant 10.

Figure 11:
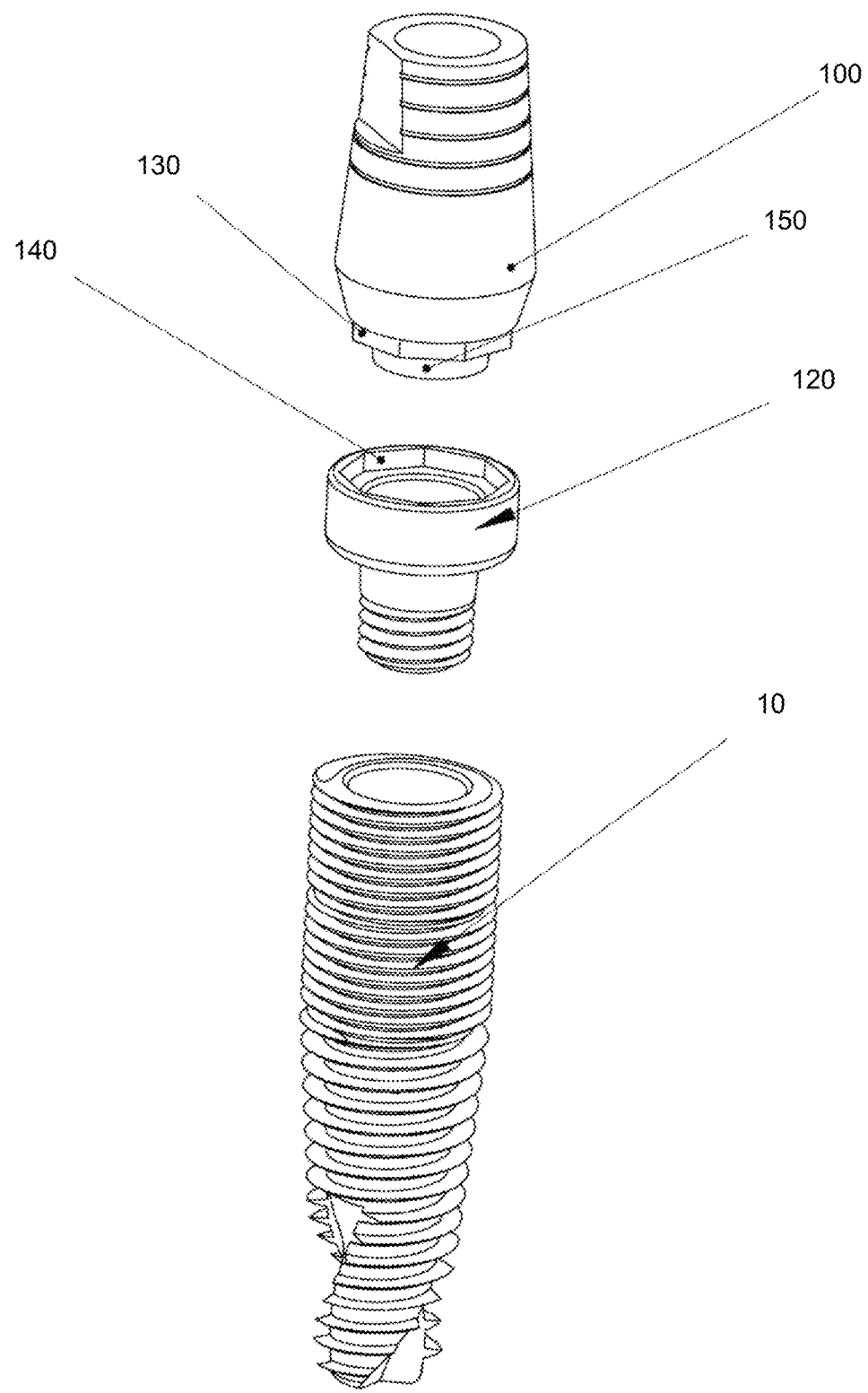
FIG. 11 is a perspective view of an abutment that is to be attached to a modular dental implant, according to an embodiment of the invention.

FIG. 11 is a perspective view of abutment 100 that is to be attached to modular dental implant 10 by using an adaptor 120. Abutment 100 includes external abutment hex 130 for fastening abutment 100 to adaptor 120 and an abutment sealing surface 150. Adaptor 120 includes an internal adaptor hex 140 into which external abutment hex 130 is fastened.

Figure 12A:
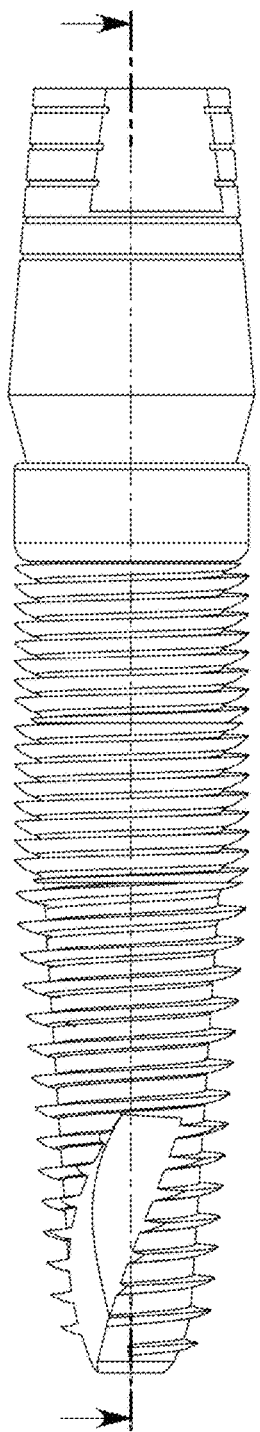
FIG. 12A is a front view and FIG. 12B is a longitudinal cross sectional view of an abutment after being attached to a modular dental implant, according to an embodiment of the invention.
Figure 12B:
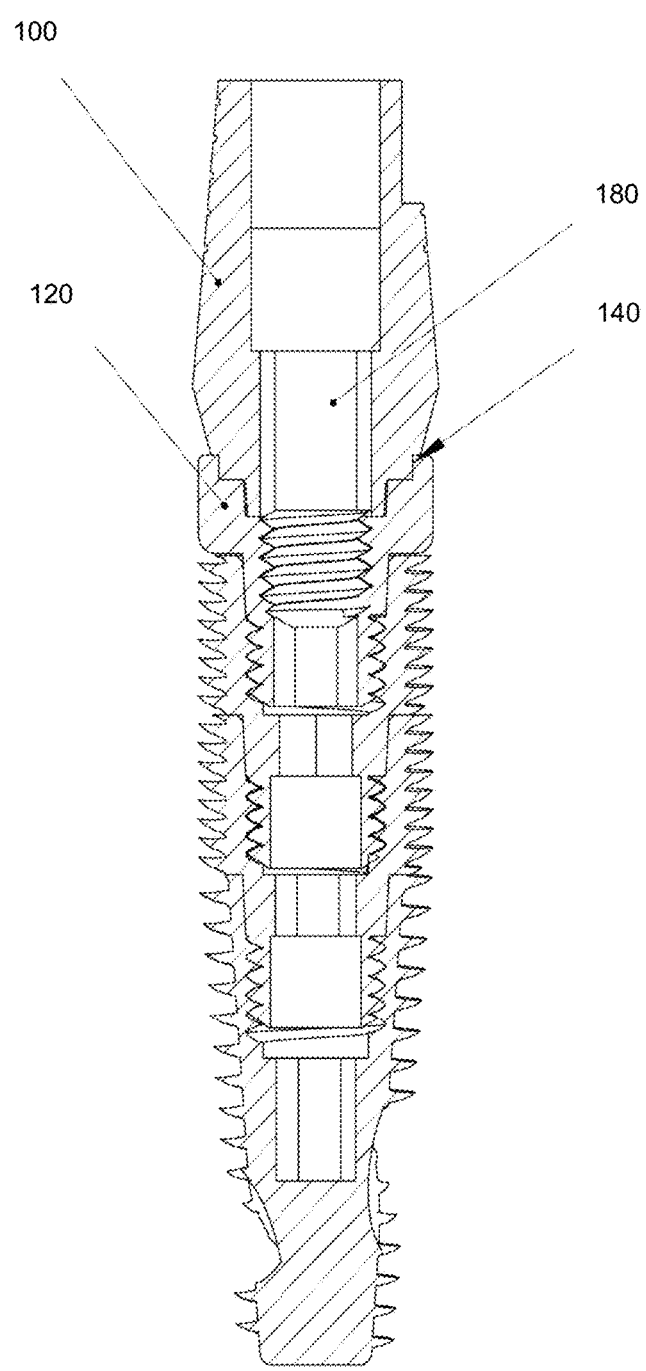

FIG. 12A is a front view and FIG. 12B is a longitudinal cross sectional view of abutment 100 after being attached to modular dental implant 10 by using an adaptor 120. Fastening screw 180 is used for fastening abutment 100 to modular dental implant 10.

Figure 13:
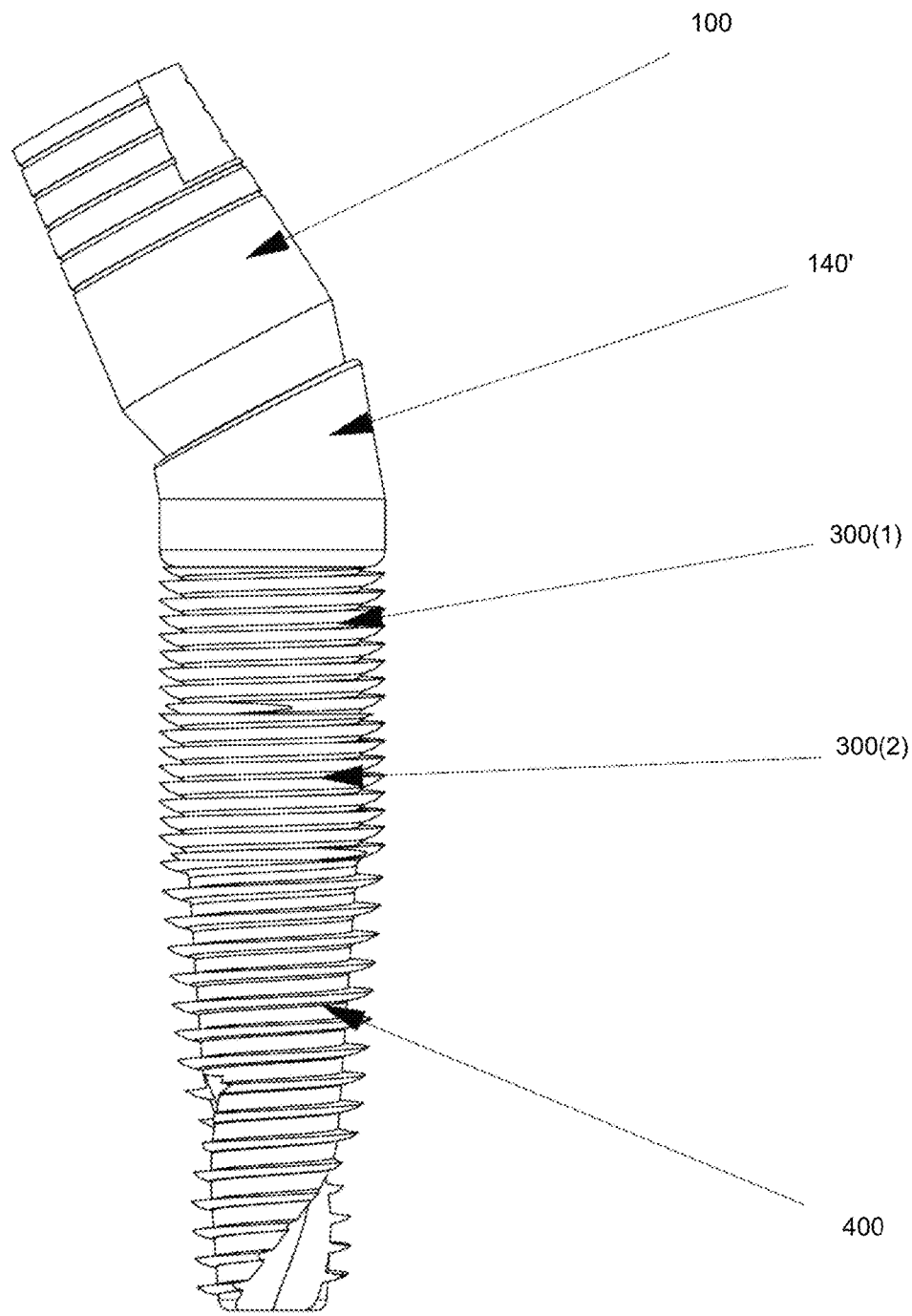
FIG. 13 is a front view of an abutment after being attached to a modular dental implant with a different adaptor, according to another embodiment of the invention.

FIG. 13 is a front view of abutment 100 after being attached to modular dental implant 10 by using an angulated adaptor 120', so that abetment 100 is inclined in relation to modular dental implant 10.

FIG. 14 is a front view of segments with different threads: sharp thread 360, square thread 360' and wide square 360".

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A modular dental implant comprising:
    (a) an implant apex comprising:
        an internal fastening surface;
    (b) at least one first hollow implant body segment that comprises:
        an internal surface having a fastening surface and at least one helical extracting thread wherein the fastening surface and the at least one helical extracting thread are distinct;
        an external fastening surface configured to be fastened to said internal fastening surface of said implant apex;
    (c) an abutment having a screw access hole, said abutment configured to be fastened to said first hollow implant body segment; and
    (d) a fastening screw configured to be screwed: (i) through said abutment and said first hollow implant body segment, and (ii) into said implant apex, when said abutment, said first hollow implant body segment, and said implant apex are fastened together.

2. The modular dental implant according to claim 1, wherein the following elements are helically-threaded:
    said internal fastening surface of said implant apex;
    said internal fastening surface of said first hollow implant body segment; and
    said external fastening surface of said first hollow implant body segment.

3. The modular dental implant according to claim 1, wherein the following elements have a detachment prevention texture that generates friction:
    said internal fastening surface of said implant apex;
    said internal fastening surface of said first hollow implant body segment; and
    said external fastening surface of said first hollow implant body segment.

4. The modular dental implant according to claim 1, further comprising a second hollow implant body segment that comprises:
    an internal fastening surface; and
    an external fastening surface configured to be fastened to said helically-threaded internal fastening surface of said first hollow implant body segment.

5. The modular dental implant according to claim 4, wherein each of said first and second hollow implant body segments further comprises:
    at least one circumferential groove; and
    at least one circumferential tongue shaped to fit into said at least one circumferential groove of the other one of said first or said second hollow implant body segments.

6. The modular dental implant according to claim 4, wherein:
    said external fastening surface of said first and second hollow implant body segments has a diameter larger than a diameter of said internal fastening surface of said first and second hollow implant body segments,
    so that said first hollow implant body segment can be fastened to said second hollow implant body segment by forcing said external fastening surface of said first hollow implant body segment to said internal fastening surface of said second hollow implant body segments.

7. The modular dental implant according to claim 1, wherein at least one of said implant apex and said first hollow implant body segment further comprises external threads configured for at least one of:
    assisting in insertion of the modular dental implant into a drilled jaw; and
    preventing undesired extraction of the modular dental implant from the jaw.

8. The modular dental implant according to claim 1, wherein:
    said implant apex further comprises:

an extractor supporting surface disposed at the bottom of said implant apex.

9. The modular dental implant according to claim 1, further comprising:
an implant neck comprising:
an external fastening surface that is substantially identical to said external fastening surface of said first hollow implant body segment,
wherein said external fastening surface of said implant neck is configured to be fastened to said internal fastening surface of said first hollow implant body segment; and
an internal abutment mount configured to provide support to said abutment,
wherein said fastening screw is further configured to be screwed through said implant neck.

10. The modular dental implant according to claim 1, wherein:
said abutment is shaped to fit into a top portion of said first hollow implant body segment.

11. The modular dental implant according to claim 1, wherein said at least one helical extracting thread is configured so that when engaged with threads of a rotating extractor brings about extraction of said first hollow segment from said hollow implant apex.

12. The modular dental implant according to claim 1, wherein said hollow implant body internal surface comprises a neck.

13. A method comprising:
providing a modular dental implant that comprises:
(a) an implant apex comprising:
an internal fastening surface;
(b) a first hollow implant body segment comprising:
an internal surface having a fastening surface and at least one helical extracting thread wherein the fastening surface and the at least one helical extracting thread are distinct;
an external fastening surface configured to be fastened to said internal fastening surface of said implant apex,
(c) an abutment having a screw access hole, said abutment configured to be fastened to said first hollow implant body segment, and
(d) a fastening screw;
fastening said external fastening surface of said first hollow implant body segment to said internal fastening surface of said implant apex; and
screwing said fastening screw: (i) through said abutment and said first hollow implant body segment, and (ii) into said implant apex, when said abutment, said first hollow implant body segment, and said implant apex are fastened together.

14. The method according to claim 13, wherein:
said modular dental implant further comprises a second hollow implant body segment that comprises:
an internal surface having a fastening surface and at least one helical extracting thread wherein the fastening surface and the at least one helical extracting thread are distinct; and
an external fastening surface configured to be fastened to said helically-threaded internal surface of said first hollow implant body segment; and
the method further comprises:
fastening said external fastening surface of said second hollow implant body segment to said internal fastening surface of said first hollow implant body segment,
wherein the screwing of said fastening screw is further through said second hollow implant body segment.

15. The method according to claim 14, wherein:
said implant apex further comprises:
an extractor supporting surface disposed at the bottom of said implant apex; and
the method further comprises using an extractor that has an extracting helical thread to extract said first hollow implant body segment by:
rotating said extractor and forcing said extractor against said extractor supporting surface of said implant apex,
thereby extracting said first hollow implant body segment.

16. The method according to claim 14, wherein when forcing said extractor against said extractor supporting surface of said implant apex,
said extractor extracting helical thread engages said at least one helical extracting thread of said first hollow implant body segment.

17. A kit comprising:
a modular dental implant that comprises:
(a) an implant apex comprising:
an internal fastening surface,
an extractor supporting surface disposed at the bottom of said implant apex;
(b) a first hollow implant body segment comprising:
an internal surface having a fastening surface and at least one helical extracting thread wherein the fastening surface and the at least one helical extracting thread are distinct;
a helically-threaded external fastening surface configured to be fastened to said helically-threaded internal fastening surface of said implant apex;
(c) an abutment having a screw access hole, said abutment configured to be fastened to said first hollow implant body segment; and
(d) a fastening screw configured to be screwed: (i) through said abutment and said first hollow implant body segment, and (ii) into said implant apex, when said abutment, said first hollow implant body segment, and said implant apex are fastened together; and
a first extractor:
having an extracting helical thread, and
configured to extract said first hollow implant body segment by:
rotating said extractor and forcing said extractor against said extractor supporting surface of said implant apex,
thereby extracting said first hollow implant body segment.

18. The kit according to claim 17, further comprising:
a second hollow implant body segment that comprises:
an internal surface having a fastening surface and at least one helical extracting thread wherein the fastening surface and the at least one helical extracting thread are distinct;
an external fastening surface configured to be fastened to said internal fastening surface of said first hollow implant body segment;
a second extractor:
having an extracting helical thread, and
configured to extract said second hollow implant body segment by:
rotating said extractor and forcing said extractor against said extractor supporting surface of said implant apex, thereby extracting said second hollow implant body segment, wherein:

said extracting helical thread of said first extractor is located at distance from a bottom of said first extractor that is different than a distance between said extracting helical thread of said second extractor and a bottom of said second extractor; and an extractor selection gauge having denotations at different distances from a bottom of said extractor selection gauge, wherein each of said denotations is indicative of a different one of said first extractor and second extractor.

19. The kit according to claim 17, wherein said extracting helical thread of said first extractor is located at distance from a bottom of said first extractor and engages said at least one helical extracting thread of said first hollow implant body segment.

* * * * *